US 11,143,641 B1

(12) United States Patent
Templeton

(10) Patent No.: US 11,143,641 B1
(45) Date of Patent: Oct. 12, 2021

(54) GAS SENSOR CALIBRATION METHOD

(71) Applicant: Vivante Health, Inc., Houston, TX (US)

(72) Inventor: Alexander Templeton, Backus, MN (US)

(73) Assignee: Vivante Health, Inc., Houston, TX (US)

( * ) Notice: Subject to any disclaimer, the term of this patent is extended or adjusted under 35 U.S.C. 154(b) by 0 days.

(21) Appl. No.: 17/222,422

(22) Filed: Apr. 5, 2021

(51) Int. Cl.
*G01N 33/00* (2006.01)
*G01N 33/497* (2006.01)
*G01N 27/12* (2006.01)

(52) U.S. Cl.
CPC ......... *G01N 33/0006* (2013.01); *G01N 27/12* (2013.01); *G01N 33/497* (2013.01); *G01N 2033/4975* (2013.01)

(58) Field of Classification Search
CPC .................................................. G01N 33/0006
See application file for complete search history.

(56) References Cited

U.S. PATENT DOCUMENTS

| | | | | |
|---|---|---|---|---|
| 4,197,089 A * | 4/1980 | Willis | ..................... | G01N 27/12 324/71.5 |
| 4,350,660 A * | 9/1982 | Robinson | ............. | G01N 27/126 338/34 |
| 4,591,414 A * | 5/1986 | Zaromb | ............. | G01N 27/4045 204/406 |
| 4,706,493 A * | 11/1987 | Chang | ..................... | G01N 27/12 340/634 |
| 5,206,511 A * | 4/1993 | Apperson | ............ | G01N 21/274 250/252.1 |
| 5,367,283 A * | 11/1994 | Lauf | ....................... | G01N 27/12 338/307 |
| 5,565,075 A * | 10/1996 | Davis | ................. | G01N 27/4045 204/291 |
| 5,606,804 A * | 3/1997 | Smith | ................... | F26B 25/009 34/261 |
| 5,629,435 A * | 5/1997 | Royster, Jr. | ........... | C07F 11/005 423/606 |
| 5,767,388 A * | 6/1998 | Fleischer | ............... | G01N 27/12 73/23.31 |

(Continued)

OTHER PUBLICATIONS

Andrea De Marcellis et al., "A Capacitance-to-Time Converter-Based Electronic Interface for Differential Capacitive Sensors", Electronics, vol. 8, No. 80, Jan. 10, 2019. (Year: 2019).*

(Continued)

*Primary Examiner* — David A. Rogers
(74) *Attorney, Agent, or Firm* — Eric P. Mirabel, JD, LLM

(57) ABSTRACT

A method of calibration of gas sensors, including breath gas sensors which are portable and for home, consumer, or medical use, wherein the calibration against samples of a measured gas having a concentration above the null value is only performed once to establish a set of calibration ratios of measured known gas concentration readings over null sample readings. Thereafter, in use, the ratio of unknown gas concentration in a test sample to a null value (preferably ambient air) is determined without recalibration, and that ratio is compared with the set of calibration ratios to determine the unknown gas concentration by interpolation or extrapolation.

16 Claims, 2 Drawing Sheets

(56) References Cited

U.S. PATENT DOCUMENTS

| | | | | |
|---|---|---|---|---|
| 7,664,607 | B2* | 2/2010 | Broy | G01N 27/404 |
| | | | | 702/24 |
| 7,716,962 | B2* | 5/2010 | Woodford | G01N 21/274 |
| | | | | 73/1.06 |
| 7,828,955 | B2* | 11/2010 | Wang | G01N 33/0054 |
| | | | | 205/780.5 |
| 8,217,355 | B1* | 7/2012 | Wong | G01N 21/3504 |
| | | | | 250/345 |
| 8,505,354 | B2* | 8/2013 | Lee | G01N 27/16 |
| | | | | 73/1.07 |
| 8,950,240 | B2* | 2/2015 | Yeh | G01N 33/0047 |
| | | | | 73/31.06 |
| 9,213,013 | B2* | 12/2015 | Zevenbergen | G01N 27/4045 |
| 9,664,633 | B2* | 5/2017 | Erdler | G01N 33/005 |
| 9,739,737 | B2* | 8/2017 | Swager | G01N 33/0047 |
| 10,145,828 | B2* | 12/2018 | Mealy, Jr. | G01D 4/004 |
| 10,724,979 | B2* | 7/2020 | Lai | G01N 33/497 |
| 10,969,371 | B2* | 4/2021 | Xie | G01N 30/64 |
| 2004/0055359 | A1* | 3/2004 | Ketler | G01N 33/0006 |
| | | | | 73/1.07 |
| 2007/0078608 | A1* | 4/2007 | Broy | G01N 33/0006 |
| | | | | 702/24 |
| 2008/0173065 | A1* | 7/2008 | Woodford | G01N 21/3504 |
| | | | | 73/1.06 |
| 2008/0251379 | A1* | 10/2008 | Mayer | G01N 27/404 |
| | | | | 204/406 |
| 2009/0247890 | A1* | 10/2009 | Hausmann | A61B 5/097 |
| | | | | 600/532 |
| 2011/0197649 | A1* | 8/2011 | Han | G01N 33/0006 |
| | | | | 73/1.06 |
| 2013/0292264 | A1* | 11/2013 | Hou | G01N 27/3272 |
| | | | | 205/775 |
| 2015/0233879 | A1* | 8/2015 | Tolmie | G01N 33/0037 |
| | | | | 128/202.22 |
| 2016/0033460 | A1* | 2/2016 | Mealy, Jr. | G01N 33/0006 |
| | | | | 73/1.06 |
| 2017/0074844 | A1* | 3/2017 | Tolmie | A61M 16/201 |
| 2018/0156766 | A1* | 6/2018 | Zeng | G01N 33/004 |
| 2018/0299406 | A1* | 10/2018 | Zhang | G01N 27/66 |
| 2019/0101515 | A1* | 4/2019 | Konieczka | G01N 33/0006 |
| 2020/0319153 | A1* | 10/2020 | Makaram | G01N 33/0008 |
| 2021/0072225 | A1* | 3/2021 | Reinstaedtler | A61B 5/0833 |

OTHER PUBLICATIONS

Marcos A. L. dos Reis et al., "Development of a Chemiresistor Sensor Based on Polymers-Dye Blend for Detection of Ethanol Vapor", Sensors, vol. 10, Mar. 29, 2010. (Year: 2010).*

Caroline Duc et al., "Hydrogen Sulfide Detection by Sensors Based on Conductive Polymers: A Review", Frontiers in Materials, Sep. 30, 2020. (Year: 2020).*

Aleksei Shaposhnik et al., "How to Detect Selectively Hydrogen and Hydrogen Containing Gases with Metal Oxide Gas Sensor Operating in Non-Stationary Thermal Regime?", Proceedings, vol. 2, Dec. 10, 2018. (Year: 2018).*

Aleksei Shaposhnik et al., "Selective Gas Detection by a Single MOX-Sensor", Proceedings, vol. 1, Aug. 25, 2017. (Year: 2017).*

* cited by examiner

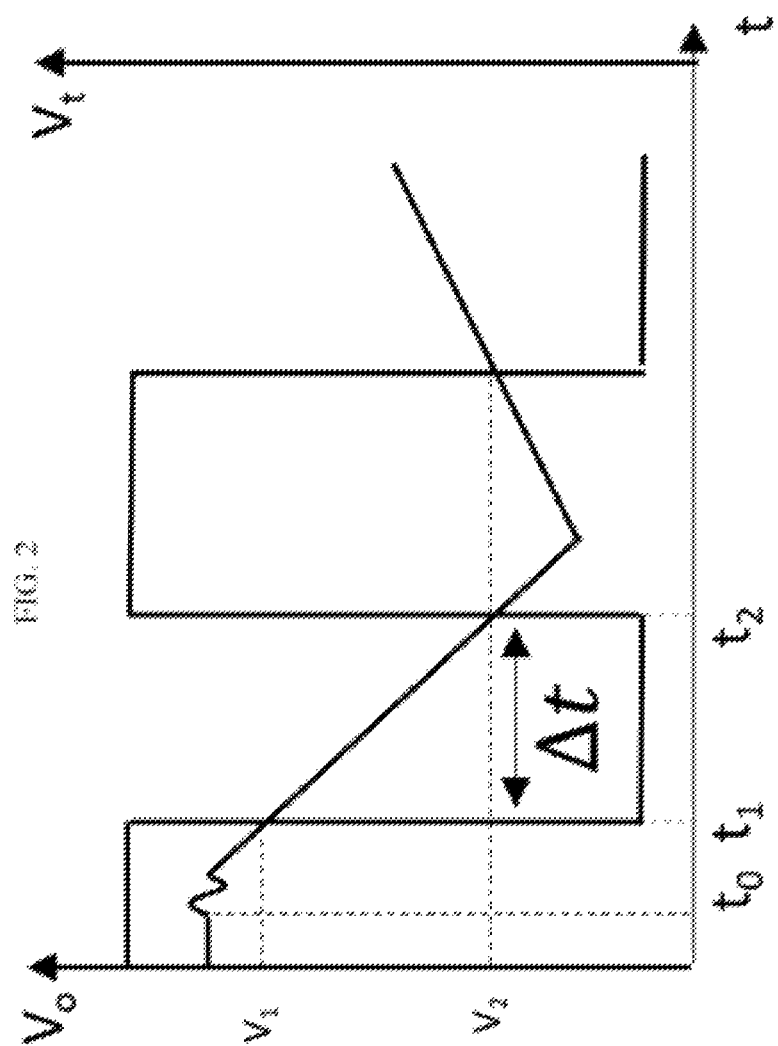

GAS SENSOR CALIBRATION METHOD

BACKGROUND

Gas sensors have a wide variety of applications including in forensics, air quality monitoring, monitoring exhaled or exuded gases and manufacturing. There are several types of gas sensors, including electrochemical gas detectors, where gases contact an electrode where the gas is either chemically oxidized or reduced. Catalytic bead sensors are commonly used to measure combustible gases. Photoionization detectors use a high-photon-energy UV lamp to ionize chemicals in the sampled gas. Infrared (IR) point sensors use radiation passing through a known volume of gas, wherein energy from the sensor beam is absorbed at certain wavelengths, depending on the properties of the specific gas. Infrared image sensors detect the same types of compounds that can be detected with infrared point detectors, and include active and passive systems. Semiconductor sensors, and metal-oxide-semiconductor sensors (MOS sensors), detect gases by a chemical reaction that takes place when the gas comes in direct contact with the sensor. Holographic gas sensors use light reflection to detect changes in a polymer film matrix containing a hologram. Since holograms reflect light at certain wavelengths, a change in their composition can generate a colorful reflection indicating the presence of a gas molecule.

One popular type of semiconductor gas sensor is a chemiresistor, which relies on variance in resistance of an electrode (often exponential variance) when a designated gas or gases react with molecules embedded in the electrode surface. The change in resistance can be processed by e.g. an integrator with the transfer function (the output based on input) indicated, and the resultant time pulse measured. Such chemiresistor sensors can have high sensitivity to detect low levels of the designated gas (1-100 ppm).

Under current protocols for chemiresistor and other gas sensors, they are calibrated at the time of use by verifying accurate readings for concentrations of the measured gas in test samples having known concentrations of the measured gas. Calibration is generally required each time an unknown sample is tested, thereby requiring access to test samples with known concentrations for each test conducted; making home use or consumer use of gas sensors inconvenient and often impractical.

Accordingly, a gas sensor for home use or consumer use is needed which does not require frequent calibration or access to known test samples for each use of the sensor.

SUMMARY

In the preferred method of the invention for calibration of gas sensors, including gas sensors which are portable and for home use or consumer use or medical use including breath gas sensors, one relies on the fact that the resulting response is unique because the ratio of readings by the gas sensor between a phase with or near a null value for the gas being detected, and a phase with a positive value for the gas being detected (i.e., where the measured gas has a concentration above the null value) is independent of absolute value of the positive value. In one example, where the gas sensor is a chemiresistor, the ratio of the resistances calculated between the two phases (R null and Rgas) is independent of resistance absolute value. Similarly, for other gas sensors, the ratio of the positive value over the null value is independent of the absolute positive value, there is no need to calibrate the gas sensor (including the chemiresistor) at the time of unknown sample testing.

The calibration method of the invention does require an initial calibration against one or more samples with known concentrations of the measured gas, where one determines a set of calibration ratios for the gas sensor with each ratio corresponding to the reading of a known gas concentration over a null sample. The set of calibration ratios is relied on for comparison with a test ratio determined for an unknown sample and using correspondence of the test ratio to a particular calibration ratio (e.g., usually determined by interpolation) to thereby determine the concentration of the measured gas in the unknown sample.

BRIEF DESCRIPTION OF THE DRAWINGS

FIG. 2 depicts the change in voltage for samples monitored at different times by a chemiresistor and circuit as in FIG. 1.

Figure 1:
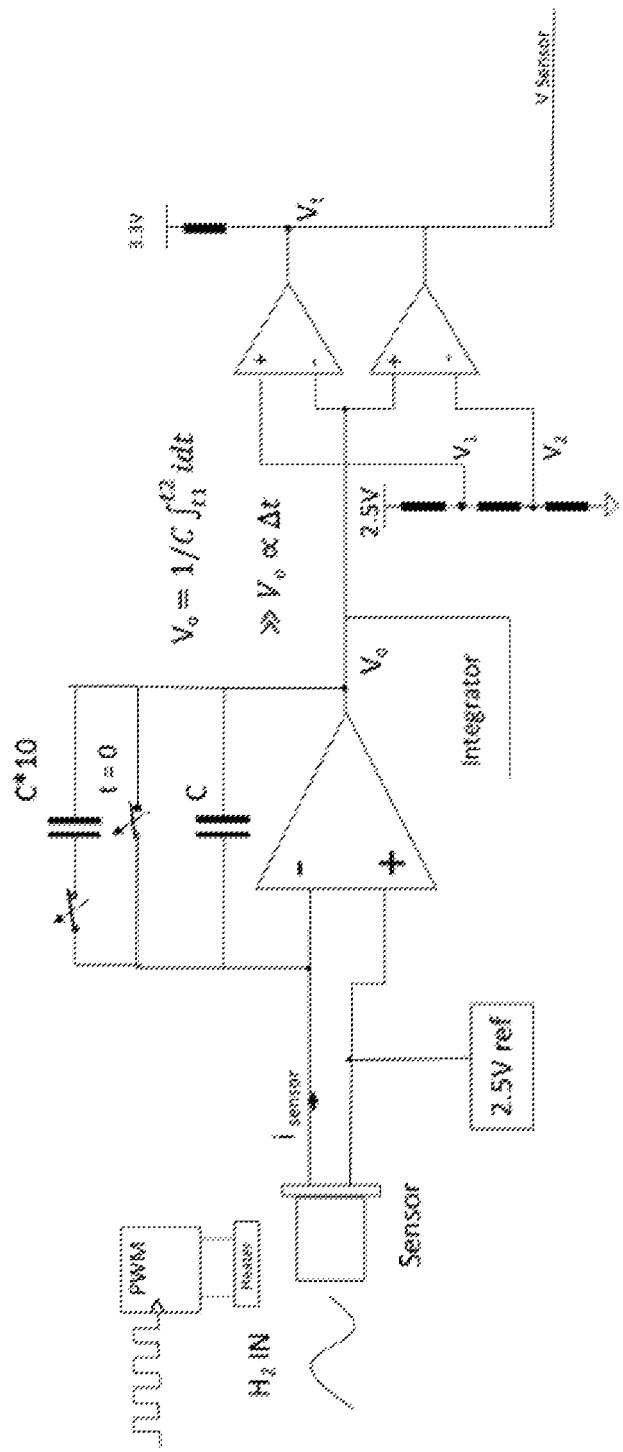
FIG. 1 is a diagram of a circuit which can be used to measure change in resistance from a chemiresistor.

The invention will now be further described with reference to the drawings.

DETAILED DESCRIPTION

All United States patents and applications noted herein are hereby incorporated by reference.

Chemiresistors operate at null resistance when no air flows over the electrode. When the measured gas is present the resistance falls from the null value by a value that is fixed by the physical area of the electrode and the semiconductor deposition process. This effectively means the resistance value of the chemiresistor always changes by a fixed amount when a given density of the designated gas is present on the electrode. This change can be expressed by the Bleasdale regression:

$$\Delta = (a+bx)^{(-1/c)}$$

where x is the designated gas concentration in ppm; and a, b and c are variables which change with the semiconductor deposition process used. According to the Bleasdale regression, the change in resistance, $\Delta$, between measurements of two different gas concentrations x, is dependent on the ratio of the two different gas concentrations rather than on their actual values.

This principle is used in calibration in the invention, by measuring first the designated gas concentration in ambient air and then the designated gas concentration in a sample including an unknown concentration of the designated gas. The sample ratio, i.e., the unknown sample over ambient air, is compared with the calibration ratios from a series of test samples with different designated gas concentrations, each ratio in the series being that of test sample reading over ambient air. The comparison of the sample and calibration ratios provides a measurement of the designated gas concentration in the sample when correspondence of the sample ratio to a particular calibration ratio representing a known designated gas concentration is determined.

The method of calibration involves a comparison with essentially a null concentration of the designated gas—that which is in ambient air—and therefore, allows reliable measurement of low gas concentrations in the sample (i.e., high sensitivity). It can provide an accurate measurement of a few ppm of the designated gas.

More significantly, the calibration ratios need only be determined once, and no calibration is needed before measuring readings from an unknown sample at the time of use, nor each time the gas sensor is used.

This method of calibration can be used to measure gas concentrations of a number of gases, including hydrogen, methane, hydrogen sulfide, ammonia, nitric oxide, methane, ethanol, isoprene, acetone, isoprene, pentane, ethane and ethylene as present in a number of sources, including atmospheric, ambient, recirculated, and exhaled gas sources.

A number of different sensors can be used with the calibration method of the invention, including the chemiresistors depicted in the drawings and described below. The sensors and the calibration method can be used to determine gas in samples from a wide variety of sources for a wide variety of purposes, including in forensics, air quality monitoring and manufacturing, as well as in determining gas concentration in breath.

Referring to FIG. 1, the circuit depicted receives current from a sensor 10, which monitors gas concentration following heating. Preferably the heater is positioned below the sensor. To avoid overheating or over-charging of the system, the circuit includes pulse wave modulation (PWM). In one embodiment, the device is heated to an internal temperature of 273° C. using its internal heater, and is then considered ready for use. The PWM is used to change the effect of the DC voltages. The voltage Vo following passing the current through integrator 20 to convert from an electrically noisy voltage signal to a low noise current, is determined from the well-known equation:

$$V_o = 1/C \int_{t1}^{t2} i\, dt$$

where Vo is equal to the voltage across the capacitor, C is equal to the capacitance of the capacitor, 1 is equal to the current flowing through the capacitor, and t is the time. The change in voltage is measured against reference voltage of 2.5V, as shown.

In the preferred embodiment, the current signal is converted to the time domain (Δt in FIG. 2) by the circuit 30. A low cost microcontroller provides the start and stop triggers and translates resultant time values (so called ticks) to a gas concentration score (see Table I; values therein representing gas concentration scores). In another embodiment, the current is measured directly by on board analog to digital converters in the microcontroller. In yet another embodiment the voltage from the sensor is measured directly by the microcontroller's analog to digital converters. In the case of embodiments of direct measurements of sensor output, the resulting resolution of these digital measurements is 12 bits at best. The preferred time domain embodiment has a 16-bit resolution and higher expected accuracy as a result.

The time domain measurement method described above offers higher resolution without adding costs; as all microcontrollers have 16-bit timers. Otherwise, to upgrade to 16-bit voltage and current measurement can be costly and requires an additional analog to digital converter.

In addition to the circuit in FIG. 1, a number of well-known circuits could be used to determine the change in resistance over time experienced by the sensor 10. Such circuits could be coupled with gas sensors to detect concentrations of a number of different gases in samples.

A $H_2$ gas sensor could be one of a number of well-known types, including as described in U.S. Pat. No. 5,367,283 & U.S. Pat. No. 9,664,633; and including the chemiresistor type made as described in A. Shaposhnik et al., Proceedings 2018 vol. 2, pp. 782 et seq. (online):

For the fabrication of gas sensing layer of the sensors, we used tin dioxide nanopowder obtained from stannic acid. For this, we added ammonia solution to the solution of tin acetate (+4) in glacial acetic acid. Stannic acid was separated from the solution in centrifuge, washed by deionized water, dried and calcinated. As a result, we obtained nano-powder of tin dioxide.

As a dopant, we used a solution of tetraamminopalladium nitrate (+2). To get printable ink, the powder consisting of a mixture of tin dioxide powder with dopant was mixed in a mortar with viscous vehicle, solution of ethylcellulose in terpineol. This ink was deposited as a thick (~10 micron thick) layer onto a substrate containing platinum electrodes and platinum microheater. The size of the substrate was of 2.5×0.5 mm. After sensing layer deposition, the substrate was dried at 423 K and annealed at 1023 K. At this temperature, fragile gel with high specific area (~100 m2/g) was formed. Palladium from the complex compound was reduced at this temperature, final palladium content in the sensing material was of 3 wt. %. After formation of the sensing layer, the substrate was packaged into TO-8 package.

Hydrogen sulfide chemiresistor sensors are also well known in the art, as described in C. Duc et al., Hydrogen Sulfide Detection by Sensors Based on Conductive Polymers: A Review Front. Mater., 30 Sep. 2020, and as described in U.S. Pat. Nos. 5,629,435; 4,197,089; 5,606,804. Methane chemiresistor sensors are also well known (see e.g., U.S. Pat. No. 4,591,414 & U.S. Pat. No. 5,767,388) as are ammonia chemiresistor sensors (U.S. Pat. No. 4,350,660 & U.S. Pat. No. 7,828,955); ethanol gas chemiresistor sensors (U.S. Pat. No. 5,606,804 & U.S. Pat. No. 4,706,493); nitric oxide chemiresistor sensors (U.S. Pat. No. 5,565,075); acetone sensors (U.S. Pat. No. 8,950,240); sensors for acetone and isoprene (U.S. Pat. No. 10,724,979); sensors for pentane (US Publ'n No. 20090247890); sensors for ethane (U.S. Pat. No. 5,606,804); and sensors for ethylene (U.S. Pat. No. 9,739,737 & U.S. Pat. No. 9,213,013).

In the example in Table I below, the gas measured using the circuit in FIG. 1 was hydrogen ($H_2$) in breath. Nevertheless, the same calibration method and circuit described herein could be used to measure the concentration of any other gas in breath or in other sample sources, with an appropriate sensor.

In Table I, after finding calibration ratios using sources with known hydrogen concentrations to establish a table or equational references (as above), one first tests the system with air. One then performs a test on a source with a higher hydrogen gas concentration, like breath. The resistance measured lowers over a 5 second period, as shown by the decreasing counts in Table I in each column, with the lowest resistance reading (the row marked "lowest" in Table I) being considered reliable, and that reading being applied as the result from the sample used to determine the hydrogen gas concentration by comparison with the calibration ratios, previously tested.

Another test using air was performed for each sample (each column in Table I) as indicated by the readings in the rows marked 4, 3, 2, 1 and Ro. These time count readings are higher, indicating a higher resistance in air than in the samples with higher hydrogen concentrations.

TABLE 1

| 2020 Jul. 20 Test data | | | | | | | | | |
|---|---|---|---|---|---|---|---|---|---|
| Mode 0 | | | | | | | | | |
| Device | A40C | | | 10 ppm | | | | | |
| Frequency | 8 | | | | | | | | |
| Flow Rate | 200 ml/min | | | | | | | | |
| Time | | 9:30 | 10:30 | 11:30 | 13:30 | 14:30 | 15:30 | 16:30 | 17:30 |
| With air | | 1st with H2 | 2nd with H2 | 3rd with H2 | 4th with H2 | 5th with H2 | 6th with H2 | 7th with H2 | 8th with H2 |
| | | 0 | 0 | 0 | 0 | 0 | 0 | 0 | 0 |
| | breathe | 28337 | 34169 | 29305 | 31750 | 31337 | 21657 | 41012 | 22292 |
| 1 sec | | 27021 | 32890 | 27100 | 32061 | 31540 | 18657 | 38367 | 22447 |
| | | 23163 | 28412 | 23369 | 32194 | 28119 | 16413 | 33170 | 20881 |
| | | 20722 | 25544 | 21136 | 32278 | 24713 | 15213 | 29842 | 18352 |
| | | 19278 | 24124 | 19841 | 31115 | 22570 | 14418 | 27828 | 16592 |
| | | 18335 | 23385 | 19032 | 27792 | 21182 | 13893 | 26535 | 15540 |
| | | 17729 | 22954 | 18591 | 25082 | 20393 | 13645 | 25685 | 14792 |
| | lowest | 17311 | 22714 | 18242 | 23271 | 19920 | 13517 | 25162 | 14281 |
| | | 0 | 0 | 0 | 0 | 0 | 0 | 0 | 0 |
| | | 0 | 0 | 0 | 0 | 0 | 0 | 0 | 0 |
| | | 0 | 0 | 0 | 0 | 0 | 0 | 0 | 0 |
| | | 0 | 0 | 0 | 0 | 0 | 0 | 0 | 0 |
| | | 0 | 0 | 0 | 0 | 0 | 0 | 0 | 0 |
| | | 0 | 0 | 0 | 0 | 0 | 0 | 0 | 0 |
| | 4 | 27523 | 8169 | 28300 | 30138 | 29784 | 10492 | 9731 | 10828 |
| | 3 | 28159 | 33713 | 29031 | 31172 | 30866 | 21453 | 40338 | 22119 |
| | 2 | 28131 | 33787 | 29082 | 31279 | 30955 | 21453 | 40307 | 22113 |
| | 1 | 28207 | 33950 | 29116 | 31472 | 31091 | 21501 | 40566 | 22192 |
| | r0 | 28303 | 34061 | 29269 | 31613 | 31206 | 21532 | 40804 | 22271 |
| | 0 | 10 | 9 | 10 | 6 | 9 | 10 | 10 | 9 |

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "including", containing", etc. are to be read expansively and without limitation. The methods and processes illustratively described herein suitably may be practiced in differing orders of steps, and that they are not necessarily restricted to the orders of steps indicated herein or in the claims. It is also noted that as used herein and in the appended claims, the singular forms "a," "an," and "the" include plural reference, and the plural include singular forms, unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The invention has been described broadly and generically herein. Each of the narrower species and subgeneric groupings falling within the generic disclosure also form part of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method of measuring a target gas concentration in an unknown sample by a gas sensor, where the gas sensor is calibrated once and then need not be calibrated at the time of measuring said gas concentration, comprising:
   a) establishing at least one calibration sample reading on the gas sensor for a calibration sample with a known concentration of target gas;
   b) establishing with the gas sensor a null reading for a first null sample with a concentration of target gas near zero;
   c) determining a calibration ratio of the calibration sample reading and the null sample reading;
   d) establishing an additional null reading on the gas sensor for a second null sample with a concentration of target gas near zero;
   e) determining a test sample reading on the gas sensor for a test sample with an unknown concentration of the target gas;
   f) determining a test ratio of the test sample reading and the additional null reading; and
   g) comparing the test ratio to the calibration ratio to determine the concentration of the target gas in the unknown sample by extrapolation or interpolation.

2. The method of claim 1 wherein several calibration sample readings are determined for several calibration samples each with a different known concentration of target gas, and several calibration ratios are determined from each calibration sample reading over a null reading, and the test ratio is compared with the calibration ratios to determine the target gas concentration in the test sample by interpolation.

3. The method of claim 1 wherein the gas sensor is a catalytic bead sensor, a photoionization detector, an infrared point detector, an infrared image sensor, a semiconductor sensor, or a holographic gas sensor.

4. The method of claim 1 wherein the gas sensor is a chemiresistor.

5. The method of claim 4 wherein several readings are determined over a specified period for both the calibration sample chemiresistor readings and the test sample chemiresistor readings.

6. The method of claim 5 wherein the chemiresistor readings are represented by a change in a time signal.

7. The method of claim 1 wherein the target gas is hydrogen, methane, hydrogen sulfide, ammonia, nitric oxide, methane, ethanol, isoprene, acetone, isoprene, pentane, ethane or ethylene.

8. The method of claim 1 wherein the test sample is exhaled air.

9. The method of claim 1 wherein the first and second null samples are atmospheric, ambient or recirculated air.

10. The method of claim 1 wherein the steps d to g are performed several times with additional different null samples and test samples, but steps a to c are only performed once.

11. A method of measuring a target gas concentration in an unknown sample by a chemiresistor gas sensor, where the chemiresistor is calibrated once and then need not be calibrated at the time of measuring said gas concentration, comprising:

a) establishing at least one calibration sample reading on the chemiresistor for a calibration sample with a known concentration of target gas;

b) establishing with the chemiresistor a null reading for a first null sample with a concentration of target gas near zero;

c) determining a calibration ratio of the calibration sample reading and the null sample reading;

d) establishing an additional null reading on the chemiresistor for a second null sample with a concentration of target gas near zero;

e) determining a test sample reading on the chemiresistor for a test sample with an unknown concentration of the target gas;

f) determining a test ratio of the test sample reading and the additional null reading;

g) comparing the test ratio to the calibration ratio to determine the concentration of the target gas in the unknown sample by extrapolation or interpolation; and h) repeating steps d to g for a third null sample with a concentration of target gas near zero and determining a second test sample reading on the chemiresistor for a second test sample with an unknown concentration of the target gas to determine the test ratio, and comparing the test ratio to the calibration ratio without repeating steps a to c.

12. The method of claim 11 wherein the chemiresistor readings are represented by a change in a time signal.

13. The method of claim 11 wherein the target gas is hydrogen, methane, hydrogen sulfide, ammonia, nitric oxide, methane, ethanol, isoprene, acetone, isoprene, pentane, ethane or ethylene.

14. The method of claim 11 wherein the test sample is exhaled air.

15. The method of claim 11 wherein the first and second null samples are atmospheric, ambient or recirculated air.

16. The method of claim 11 wherein the step h is performed several times with additional different nul samples and test samples, but steps a to c are only performed once.

* * * * *